(12) United States Patent
Narasimhan et al.

(10) Patent No.: US 10,571,454 B2
(45) Date of Patent: Feb. 25, 2020

(54) METHOD OF BOARD LUMBER GRADING USING DEEP LEARNING TECHNIQUES

(71) Applicant: LUCIDYNE TECHNOLOGIES, INC., Corvallis, OR (US)

(72) Inventors: Revathy Narasimhan, Santa Clara, CA (US); Patrick Freeman, Corvallis, OR (US); Hayden Michael Aronson, Corvallis, OR (US); Kevin Johnsrude, Corvallis, OR (US); Chris Mosbrucker, Philomath, OR (US); Dan Robin, Albany, OR (US); Ryan T. Shear, Corvallis, OR (US); Joseph H. Weintraub, Eugene, OR (US); Eric N. Mortensen, Albany, OR (US)

(73) Assignee: Lucidyne Technologies, Inc., Corvallis, OR (US)

(*) Notice: Subject to any disclaimer, the term of this patent is extended or adjusted under 35 U.S.C. 154(b) by 0 days.

(21) Appl. No.: 16/082,103

(22) PCT Filed: Mar. 5, 2018

(86) PCT No.: PCT/US2018/020970
§ 371 (c)(1),
(2) Date: Sep. 4, 2018

(87) PCT Pub. No.: WO2018/169712
PCT Pub. Date: Sep. 20, 2018

(65) Prior Publication Data
US 2019/0227049 A1    Jul. 25, 2019

Related U.S. Application Data

(60) Provisional application No. 62/470,732, filed on Mar. 13, 2017.

(51) Int. Cl.
*G01N 33/46* (2006.01)
*G06T 7/00* (2017.01)
(Continued)

(52) U.S. Cl.
CPC .......... *G01N 33/46* (2013.01); *G06K 9/3233* (2013.01); *G06K 9/6202* (2013.01); *G06N 7/005* (2013.01);
(Continued)

(58) Field of Classification Search
None
See application file for complete search history.

(56) References Cited

U.S. PATENT DOCUMENTS 10,019,657 B2 * 7/2018 Lin ..................... G06K 9/66
2005/0031158 A1   2/2005 Biernacki et al.
(Continued)

OTHER PUBLICATIONS

Wenshu, L.—"Study on Wood Board Defect Detection Based on Artificial Neural Network"—The Open Automation and Control Systems Journal 2015, pp. 290-295 (Year: 2015).*
(Continued)

*Primary Examiner* — Bernard Krasnic
(74) *Attorney, Agent, or Firm* — Stoel Rives LLP (57) ABSTRACT

A method of board lumber grading is performed in an industrial environment on a machine learning framework configured as an interface to a machine learning-based deep convolutional network that is trained end-to-end, pixels-to-pixels on semantic segmentation. The method uses deep learning techniques that are applied to semantic segmentation to delineate board lumber characteristics, including their sizes and boundaries.

10 Claims, 12 Drawing Sheets

(51) Int. Cl.
G06K 9/32 (2006.01)
G06K 9/62 (2006.01)
G06N 7/00 (2006.01)
G06N 3/04 (2006.01)

(52) U.S. Cl.
CPC .......... *G06T 7/0004* (2013.01); *G06N 3/0418* (2013.01); *G06T 2207/30161* (2013.01)

(56) References Cited

U.S. PATENT DOCUMENTS

| | | |
|---|---|---|
| 2007/0246125 A1 | 10/2007 | Latos |
| 2016/0189009 A1 | 6/2016 | Tran et al. |
| 2018/0108137 A1* | 4/2018 | Price .................. G06T 7/11 |
| 2018/0114071 A1* | 4/2018 | Wang ............. G06K 9/00744 |

OTHER PUBLICATIONS

Estevez, P.A.—"Selection of Features for the Classification of Wood Board Defects"—IEE 1999, pp. 347-352 (Year: 1999).*
Hou, S.—"Deeply Exploit Depth Information for Object Detection"—arXiv—May 8, 2016—pp. 1-9 (Year: 2016).*
Qi, D.—"Research on Recognition of Wood Defect Types Based on Back-Propagation Neural Network"—IEEE 2008, pp. 2589-2594 (Year: 2008).*
Badrinarayanan, et al., "SegNet: A Deep Convolutional Encoder-Decoder Architecture for Image Segmentation," Machine Intelligence Lab, Department of Engineering, University of Cambridge, UK, Oct. 10, 2016, 14 pages.
Git repository for source code of Caffe: a fast open framework for deep learning. Retrieved on Aug. 17, 2018 from Internet: <https://github.com/BVLC/caffe>, 2 pages.
Git repository for source code of Implementation of SegNet: A Deep Convolutional Encoder-Decoder Architecture for Semantic Pixel-Wise Labelling. Retrieved on Aug. 17, 2018 from the Internet: <https://github.com/alexgkendall/caffe-segnet>, 2 pages.
Paszke, et al., "ENet: A Deep Neural Network Architecture for Real-Time Semantic Segmentation," Faculty of Mathematics, Informatics and Mechanics University of Warsaw, Poland, Jun. 7, 2016, 10 pages.
Ruoxu Ren, Terence Hung, and Kay Chen Tan, Fello, IEEE; A Generic Deep-Learning-Based Approach for Automated Surface Inspection; pp. 1-12; Feb. 24, 2017; IEEE; IEEE Transactions on Cybernetics.†
Xavier Gilbert, Vishal M. Patel, and Rama Chellappa; Material Classification and Semantic Segmentation of Railway Track Images with Deep Convolutional Neural Networks; pp. 621-625; Dec. 10, 2015; IEEE.†
Pascal Kaiser, Jan Wegner, Aurelien Lucchi, Martin Jaggi, Thomas Hofmann, and Konrad Schindler; Learning Aerial Image Segmentation From Online Maps; pp. 1-15; Jul. 21, 2017; IEEE; IEEE Transactions on Geoscience and Remote Sensing.†
Luiz G. Hafemann, Luiz S. Oliveira, and Paulo Cavalin; Forest Species Recognition using Deep Convolutional Neural Networks; pp. 1103-1107; Dec. 8, 2014; IEEE; 22nd International Conference on Pattern Recognition.†
Gonzalo A. Ruz , Pablo A. Estvez, and Pablo A. Ramrez; Automated visual inspection system for wood defect classification using computational intelligence techniques; pp. 163-172; Feb. 2009; International Journal of Systems Science.†
Matti Niskanen; A Visual Training Based Approach to Surface Inspection; pp. 1-132; Jun. 18, 2003; Oulu University Press; Oulu.†
Min Bai, Raquel Urtasun; Deep Watershed Transform for Instance Segmentation; pp. 1-9; Nov. 24, 2016; https://arxiv.org; arXiv:1611.08303v1 [cs.CV] Nov. 24, 2016.†

\* cited by examiner
† cited by third party

METHOD OF BOARD LUMBER GRADING USING DEEP LEARNING TECHNIQUES

RELATED APPLICATION

This application claims benefit of U.S. Patent Application No. 62/470,732, filed Mar. 13, 2017.

COPYRIGHT NOTICE

© 2018 Lucidyne Technologies, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

The disclosed method of board lumber grading uses deep learning techniques that are applied to semantic segmentation to delineate board lumber characteristics, including their sizes and boundaries.

BACKGROUND INFORMATION

Prior art wood characteristics detection systems require experts using rules, image processing techniques, or combinations of them. These extracted features are often used as inputs to machine learning algorithms. However, the effort to derive and select a minimum set of extracted features for use in the detection process to maximize accuracy is difficult, time consuming, and not guaranteed for accuracy. The introduction of deep learning has removed a need to perform these tasks because they are done automatically as part of the learning process.

Grading board lumber defects requires that many wood characteristics, for example, knots be identified no matter what their orientation in the board (generalization). The effects of a knot on the strength of a board depend on how close the knot is to the edge and how much clear wood it displaces (location and size). It is much more difficult to teach a computer to grade board lumber than it is to teach a person. Human beings have billions of brain connections that make them experts in pattern matching. After inspecting many thousands of knots, a person can discriminate from 16 ft. (4.88 m) away the difference between a #1 knot and a #2 knot on a 2 in. (5 cm)×4 in. (10.2 cm) board.

Computer vision systems must be programmed to identify a knot. Knot heads are mostly, but not always, ovals and circles. Knots sometimes have a blonde ring. Knot edges can be obscured by pitch and stain. For dimension lumber, knot heads have to be associated with other knot heads on different faces. A person learns this task by observations that make an image in the person's mind, which filters out unimportant distractors and emphasizes significant points. It is difficult to program a computer to carry out this process.

Computers process numbers, and people process images. There is nothing in the numbers that indicates whether a particular object is important. The computer vision system looks at everything and tries to discover knots in a vast set of numbers. A computer programmer of a computer vision system attempts to anticipate all possible presentations of wood characteristics, such as knots, and then gives explicit program instructions as to how to handle exceptional cases. Modifications to programs are exhaustively tested to ensure that any changes made result in actual improvement. In spite of these difficulties, automatic grading systems introduced during the past ten years do acceptable work but are fragile and need constant improvement and maintenance.

SUMMARY OF THE DISCLOSURE

The disclosed method applies deep learning algorithms to detect characteristics in wood for grading board lumber in an industrial environment. The method of board lumber grading is performed on a machine learning framework. Caffe is a preferred fast, open deep learning framework configured as an interface to a machine learning-based deep convolutional network that is trained end-to-end, pixels-to-pixels, on semantic segmentation. Semantic segmentation classifies a collection or blob of pixels to locate edges and thereby give shape to a characteristic in wood. The collection of pixels characterized is based on examples given in training. Perceiving at once by example all pixels in a collection of pixels, semantic segmentation produces low resolution features for accurate wood characteristic boundary localization at the blob level. SegNet is a preferred neural network architecture for semantic pixel-wise segmentation that is supported by the branch of the Caffe framework to grade wood characteristics in board lumber images.

The deep convolutional neural network architecture particularly designed for segmentation learns to decode or map low resolution image representations to pixel-wise predictions in a coarse-to-fine inference progression. The Caffe framework functioning as an encoder classification network produces low resolution image representations from images acquired during a training process.

The SegNet architecture has an encoder network and a corresponding decoder network. The encoder network provided by the Caffe framework includes 27 convolutional layers designed for object classification in accordance with the disclosed method. Each layer of data in a convolutional network is a three-dimensional array of size h×w×d, in which h and w are spatial dimensions and d is the feature or channel dimension. The first layer is the image, with pixel size h×w, and d color and other sensor channels. Locations in the higher layers correspond to the locations in the image to which they are path connected. The training process is initialized from weights trained for classification on large data sets derived from images by operation of a training processing unit. Each encoder in the encoder network performs convolution with a filter bank to produce a set of input feature maps. Boundary information is captured and stored in the encoder feature maps.

The SegNet architecture decoder network upsamples its input feature maps using stored max-pooling indices from the corresponding encoding feature maps. The resulting feature maps are convolved with a trainable decoder filter bank to produce dense feature maps. The decoder corresponding to the first encoder, which is closest to the input image and has a multi-channel encoder input, produces a multi-channel feature map that is applied to a trainable spatial Softmax classifier for pixel-wise classification. The output of the Softmax classifier is a K channel image of probabilities, in which K is the number of classes. The predicted segmentation corresponds to the class with maximum probability at each pixel. The SegNet architecture uses all of the pre-trained convolutional layer weights as pre-trained weights.

The disclosed method applying deep learning algorithms selects important features during training without human intervention. If a new circumstance is discovered in the field, it is necessary only to add the new example and rerun the training procedure. The deep learning program will adjust the learned weight of each member of a current feature set while perhaps discovering additional features to make the correct decision. In essence, it is not the computer programmer who decides what is important. The deep learning program decides for itself what is important and can discover subtle discriminations that a human computer programmer might miss. The deep learning program is more robust, and maintenance is much easier.

Additional aspects and advantages will be apparent from the following detailed description of preferred embodiments, which proceeds with reference to the accompanying drawings.

DETAILED DESCRIPTION OF PREFERRED EMBODIMENTS

The disclosed method preferably uses the Caffe deep learning open framework supporting the SegNet semantic segmentation architecture to detect defining characteristics of board lumber. The Caffe framework uses fully convolutional networks for pixel prediction in the semantic segmentation application, performing inference, for example, at less than 6-seconds/image prediction for all four sides of a 16 ft. (4.9 m) long, 2 in. (51 mm)×8 in. (204 mm) board of wood. Although the Caffe deep learning framework is used in describing a preferred embodiment of the disclosed method, other deep learning framework architectures could be used. A suitable deep learning framework architecture has building blocks for assembling deep network convolutional layers, max-pooling layers, and encoder and decoder networks designed for object classification.

The deep learning process for board lumber wood characteristics entails downloading the source code for the Caffe framework from https://github.com/BVLC/caffe and the SegNet source code from https://github.com/alexkendall/caffe-segnet. A lumber grader labels images for training, and a machine learning specialist selects a model, learning rate (and other hyperparameters), and batch size. A machine learning specialist trains the system and repeatedly evaluates the solution until an acceptable error rate is achieved.

The Caffe framework models are complete machine learning systems for inference and learning. The computation follows from the model definition for each class of wood characteristics. In one example, classes of wood characteristics include knot qualities or defects. Model definition entails presenting input data information relating to many thousands of wood specimen images. The input data information for use by the Caffe framework is that which is needed to run on a central processing unit (CPU), such as an Intel®8 Core™ i7 processor, or a graphics processing unit (GPU), such as an NVidia P40 GPU, for training. An application specific integrated circuit (ASIC) or field programmable gate array (FPGA) may be suitable alternatives to a GPU. The wood specimen images show image patterns of different knots sought to be identified. Several classes of knot defects can appear on a single wood specimen image. The images of the defects are labeled by blob overlays placed around them, and are multi-channeled, including three video channels from an RGB camera, a Tracheid sensor, a Geometric sensor, a Throughboard sensor, and a decay (T3) sensor. The Caffe framework trains the deep learning system by applying the wood specimen images to the convolutional neural network and assigning a set of weights for the pixels. A deep learning algorithm implemented by the Caffe framework generalizes by establishing a set of weights that reclassify the wood specimen image data presented. This inference and learning process entails thousands of iterations in the training process to minimize error.

Figure 1:
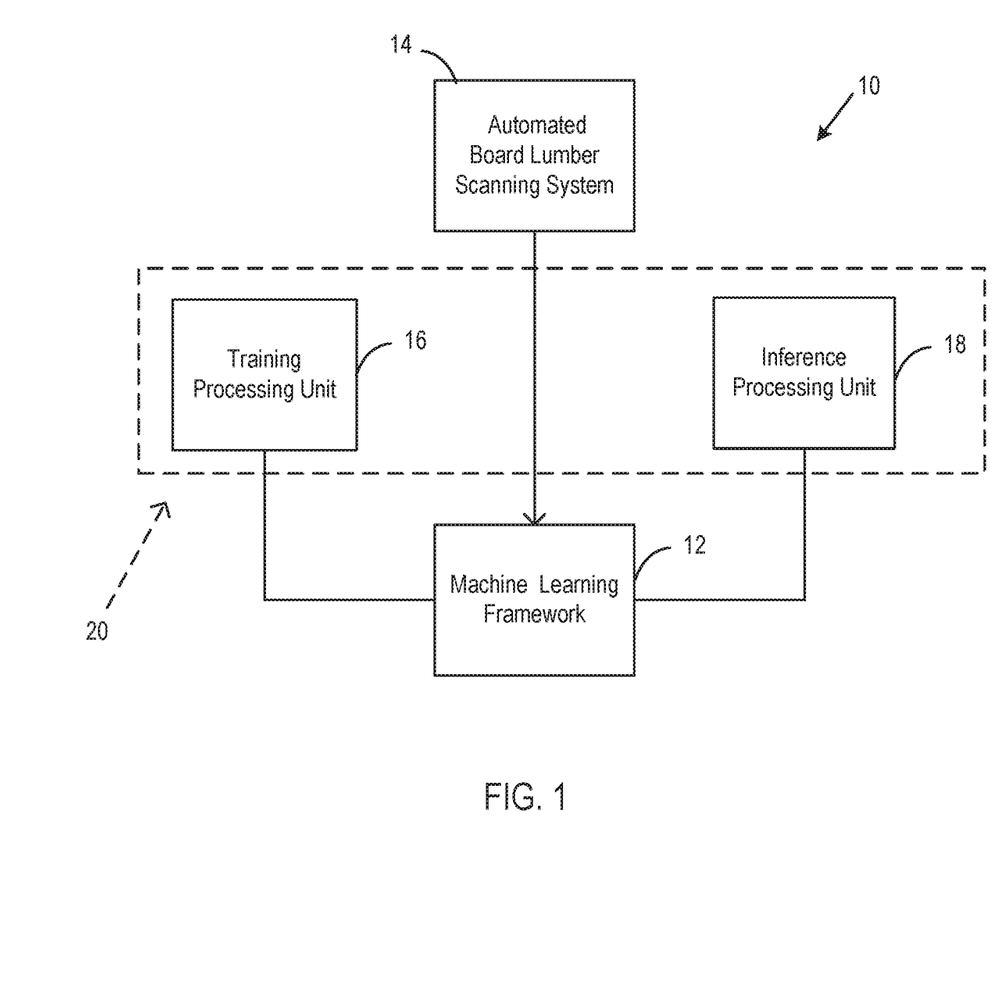
FIG. 1 is a block diagram showing the components of a system for practicing the disclosed method of board lumber grading using deep learning techniques.

FIG. 1 is a block diagram showing the components of a system 10 for practicing a preferred embodiment of the disclosed method of board lumber grading performed on a machine learning framework 12.

Machine learning framework 12, which is preferably the Caffe deep learning framework, receives wood specimen image information from an automated board lumber scanning system 14. Automated scanning system 14 scans multiple wood specimens to produce raw image data representing multiple wood specimen images that identify wood characteristics of the wood specimens. A labeling process performed preferably by a certified lumber grader entails analysis of the multiple wood specimen images to enable creation of a definition specifying classes of wood characteristics that the lumber grader sees on the board lumber. An extraction process carried out by a CPU on the labeled data creates input layer image pixel data that are format-ready as respects compatibility with machine learning framework 12 to perform the training process. The input layer pixel data represent classes of the wood characteristics within specified boundaries at known locations of regions of the multiple wood specimens. Machine learning framework 12 supports a training processing unit 16 on which a set of deep learning algorithms developed to train a convolutional neural network operates to perform semantic segmentation on the format-ready input layer pixel data. Performing semantic segmentation determines network learned weights for collections of pixels corresponding to the regions of each of the multiple wood specimens. Edge information is included in the network learned weights. Machine learning framework 12 supports an inference processing unit 18 that receives raw image data representing images of a non-labeled scanned milled board exhibiting wood characteristic features. Inference processing unit 18 delivers the raw image data to the trained convolutional neural network, which produces a series of probability maps corresponding to different ones of the classes of wood characteristics. The series of probability maps assists in developing a solution identifying which ones of the milled board features belong to classes of wood characteristics and specifying the classes to which the identified milled board features belong. Each of training processing unit 16 and inference processing unit 18 includes functionality of a CPU for formatting and similar data organization tasks and capability of a GPU for fast processing of large quantities of data, which the set of deep learning algorithms manipulates.

Training processing unit 16 and inference processing unit 18 are encompassed by a dashed line box 20 to indicate that they may be separate processing units or combined in a single integrated processing unit. If training processing unit 16 and inference processing unit 18 are integrated as part of a single processing unit, it would have a capability to perform deep learning functions.

Detecting the defining characteristics of wood material to facilitate one or both of grading and optimizing board lumber by machine learning techniques entails labeling many example images of board lumber. In a preferred embodiment, the disclosed method is performed on system 10 trained to identify 50 classes of wood characteristics or defects for each of 13 different species of wood material. Tables 1 and 2 below list the 50 classes of wood characteristics and the 13 species of wood material, respectively. The total number of labeled board lumber faces is in the 10's of thousands.

TABLE 1

| | |
|---|---|
| KnotRed | ShakePitch |
| KnotDead | ShakeTimberBreak |
| KnotBlonde | CheckSeason |
| KnotDecayed | Pith |
| KnotBarkEncasement | Skip |
| KnotSlough | SkipStained |
| CrossGrain | BirdseyeBlonde |
| PocketPitch | BirdseyeDark |
| PocketBark | WhiteSpeck |
| StainBlue | UnsoundWood |
| StainBrown | IncipientDecay |
| StainKiln | LeafScar |
| Clear | HoneyComb |
| PlanerBurn | TornGrain |
| PlanerKnifeMark | ManHole |
| SawCuts | ManHoleCrushed |
| PitchMass | Peck |
| PitchBlack | Burl |
| AntEatenPith | FireScar |
| WormEatenPitch | KnotDistortion |
| WormHole | MineralPocket |
| BeetleHole | MineralStreak |
| Wane | Heartwood |
| WaneSmoothBark | Sapwood |
| Shake | StainSpauld |

TABLE 2

| |
|---|
| Southern Yellow Pine |
| *Radiata* Pine |
| *Ponderosa* Pine |
| Eastern White Pine |
| KD Douglas Fir |
| Green Douglas Fir |
| Spruce Pine Fir |
| White Fir |
| Hemlock |
| Green Hemlock |
| Redwood |
| Alder |
| Cedar |

Although Table 1 lists 50 classes of wood characteristics and Table 2 lists 13 species of wood material, the disclosed method is not limited to any number of classes of wood characteristics or any number of species of wood material.

Figure 2:
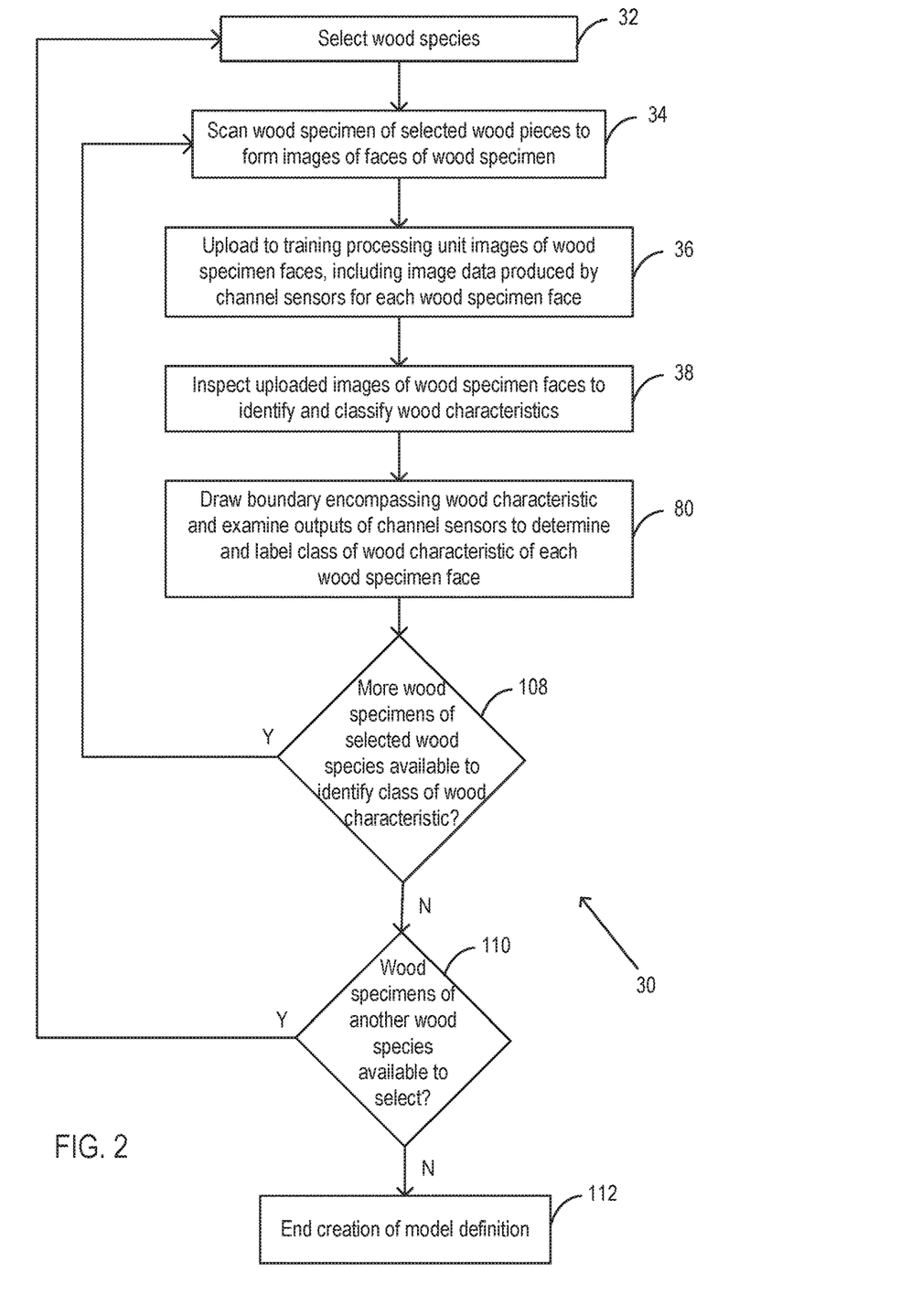
FIG. 2 is a flow diagram of the steps performed to train a machine learning system configured for one or both of board lumber grading and optimization.

FIG. 2 is a flow diagram 30 of the steps performed to train system 10 configured for one or both of board lumber grading and optimization. The process of creating a definition of wood characteristics of board lumber is accomplished by applying to training processing unit 16 multiple wood specimen images that identify the wood characteristics of wood board specimens (hereafter, "wood specimens"). With reference to FIG. 2, a process block 32 represents selection of a wood species. A process block 34 indicates that a wood specimen of the selected species is presented to and scanned by an automated board lumber scanning system for grade assessment. A GradeScan® automated scanning system is preferred in carrying out the disclosed method and is available from Lucidyne Technologies, Inc., the assignee of this patent application. The GradeScan® system is a multi-channel lumber scanning system that is implemented with a set of seven sensors that scan simultaneously all four faces of the wood specimen and produce different images of its wood material characteristics. Each sensor (also referred to as "channel sensor") represents a separate channel of the multi-channel scanner system. The seven sensors operate individually as wood characteristic detectors but provide amounts of overlapping image information that enhances and improves the overall performance of the sensors. The following description identifies each sensor of the set of sensors and some of the classes of wood characteristics the sensor detects.

An RGB color camera, which includes red, green, and blue channel sensors, allows for classification and measurement of several types of wood material defects, including, among other wood characteristics, knots, stains, heart-sap, bark, and sticker marks. A Tracheid sensor detects, among other wood characteristics, knots, distorted grain and slope of grain, surface decay, stain, pitch, blonde knots, bark, saddle wane, skip, and shake. A Geometric sensor develops profile information taken on all sides of the wood specimen to provide accurate thickness measurements. The thickness measurements indicate differential fitness and top face-to-bottom face thickness. A thin area is represented as either a differential thickness variation or a defect on a board face if the thickness variation is more frequent on one board face as compared to that on the other board face. The Geometric sensor identifies cupping and narrow boards and detects, among other wood characteristics, wane, cracks, and missing fiber. A Throughboard sensor produces an image that closely approximates the relative density of a wood board (e.g., high density indicates a knot and lower density indicates less dense fiber, holes, or decay). The Throughboard sensor facilitates cross-sectional grading and detects, among other wood characteristics, stains, decay, pith, spike knots, and bark pockets. A T3 sensor detects, among other wood characteristics, decay, including knot decay and incipient decay. The T3 sensor is that which is installed in the GradeScan® automated scanning system.

The GradeScan® system forms, for each channel sensor, an image of each of the four faces of the wood specimen. A process block 36 represents uploading to training processing unit 16 the images of the wood specimen faces, including raw image data produced by the channel sensors for each wood specimen face. The uploaded image data include image data representing the wood characteristics of the wood specimen.

A process block 38 represents acts performed to identify the classes of wood characteristics of the wood specimen. These acts are preferably carried out by the certified lumber grader who examines the image data, which are stored as input layer pixel data in training processing unit 16. Each layer of input pixel data represents the output of one of the channel sensors, which by nature of its type is suitable for detecting and thereby displaying in the image the specific wood characteristics referenced above. The lumber grader inspects the image representing each layer of input pixel data and typically uses color codes to identify particular characteristics.

FIGS. 3, 4, 5, and 6 each present two side-by-side images showing, for the same wood specimen, differences in sensor output images produced by the RGB color camera in comparison with those of each of the other channel sensors and viewed by the lumber grader.

Figure 3:
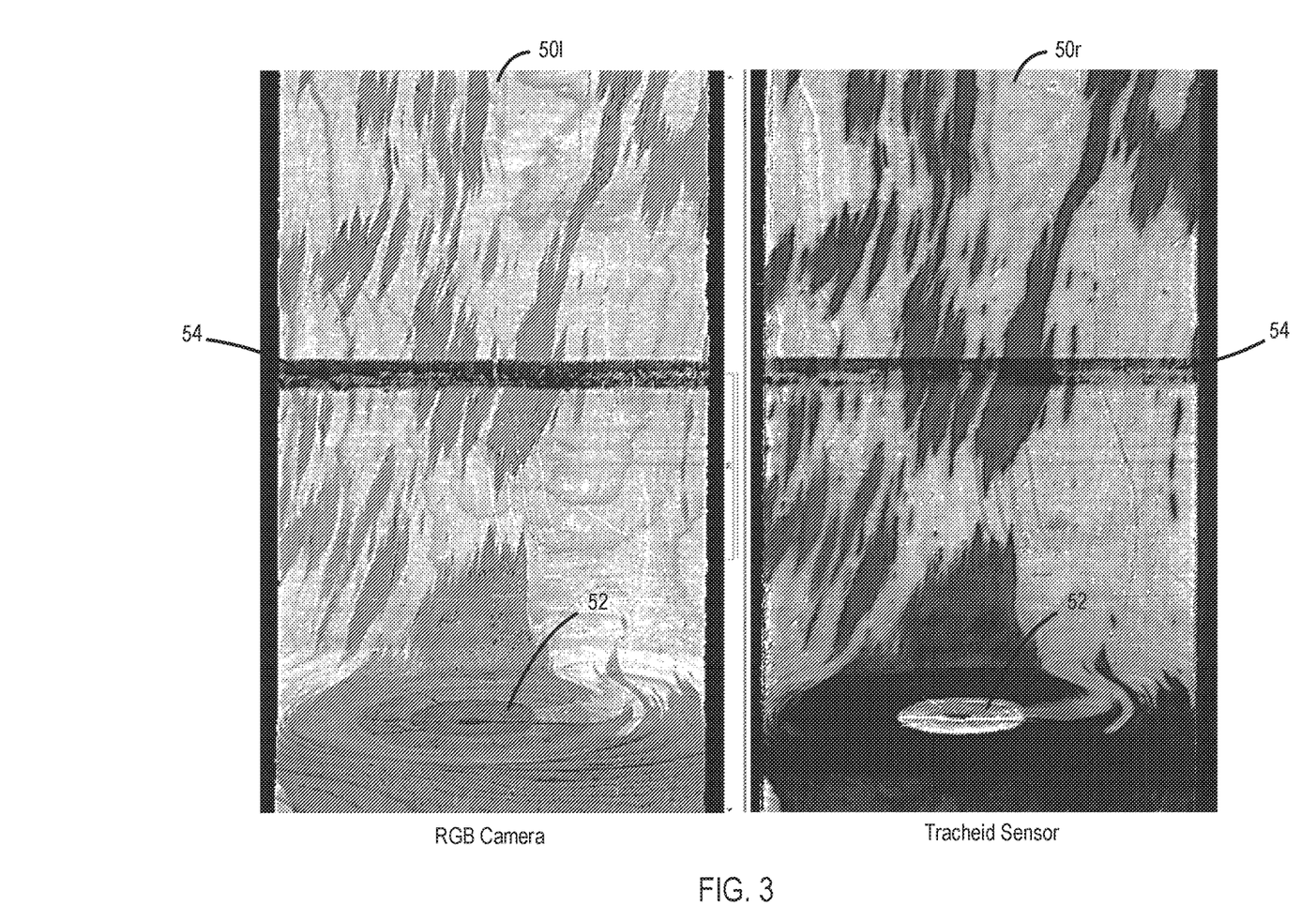
FIGS. 3, 4, 5, and 6 each present two side-by-side images showing, for the same wood specimen, differences in sensor output images produced by an RGB color camera in comparison with images produced by other channel sensors during training of the machine learning system.

FIG. 3 shows two side-by-side images of a major surface of a wood specimen, a left-side image 50l produced by an RGB color camera (but rendered as a gray scale view), and a right-side image 50r produced by a Tracheid sensor. Left-side image 50l appears in each of FIGS. 3, 4, 5, and 6. A knot 52 shown on the bottom of the two images is compressed in one direction because of the W×H=0.008 in. (0.2 mm)×0.032 in. (0.81 mm) pixel resolution. A dark horizontal line 54 dividing each image represents a planer burn on the wood specimen surface.

Figure 4:
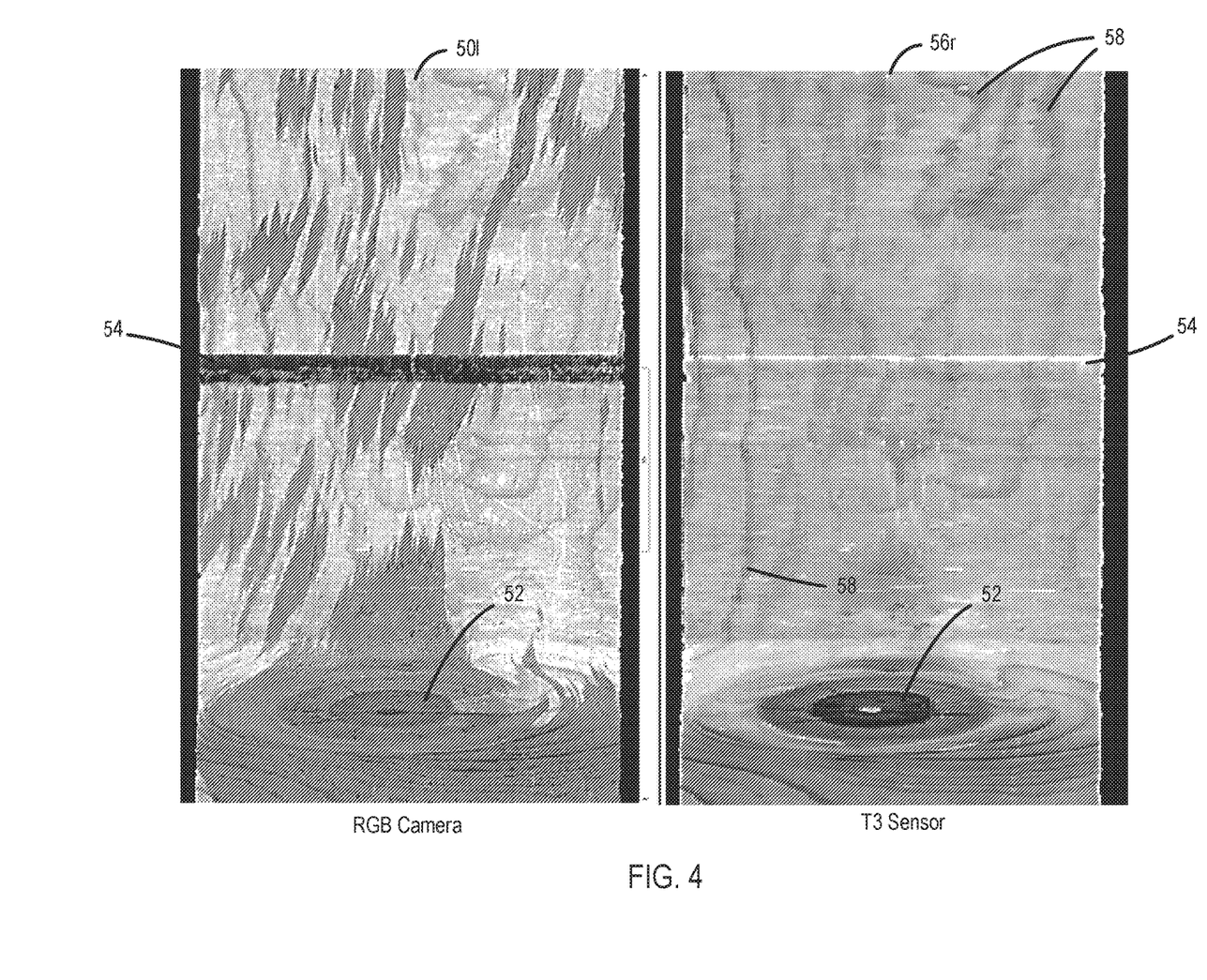

FIG. 4 shows two side-by-side images of the wood specimen, left-side image 50l and a right-side image 56r produced by a decay (T3) sensor. Natural and manufactured stains are transparent to the T3 sensor, which detects annular rings 58 and other defects otherwise hidden.

Figure 5:
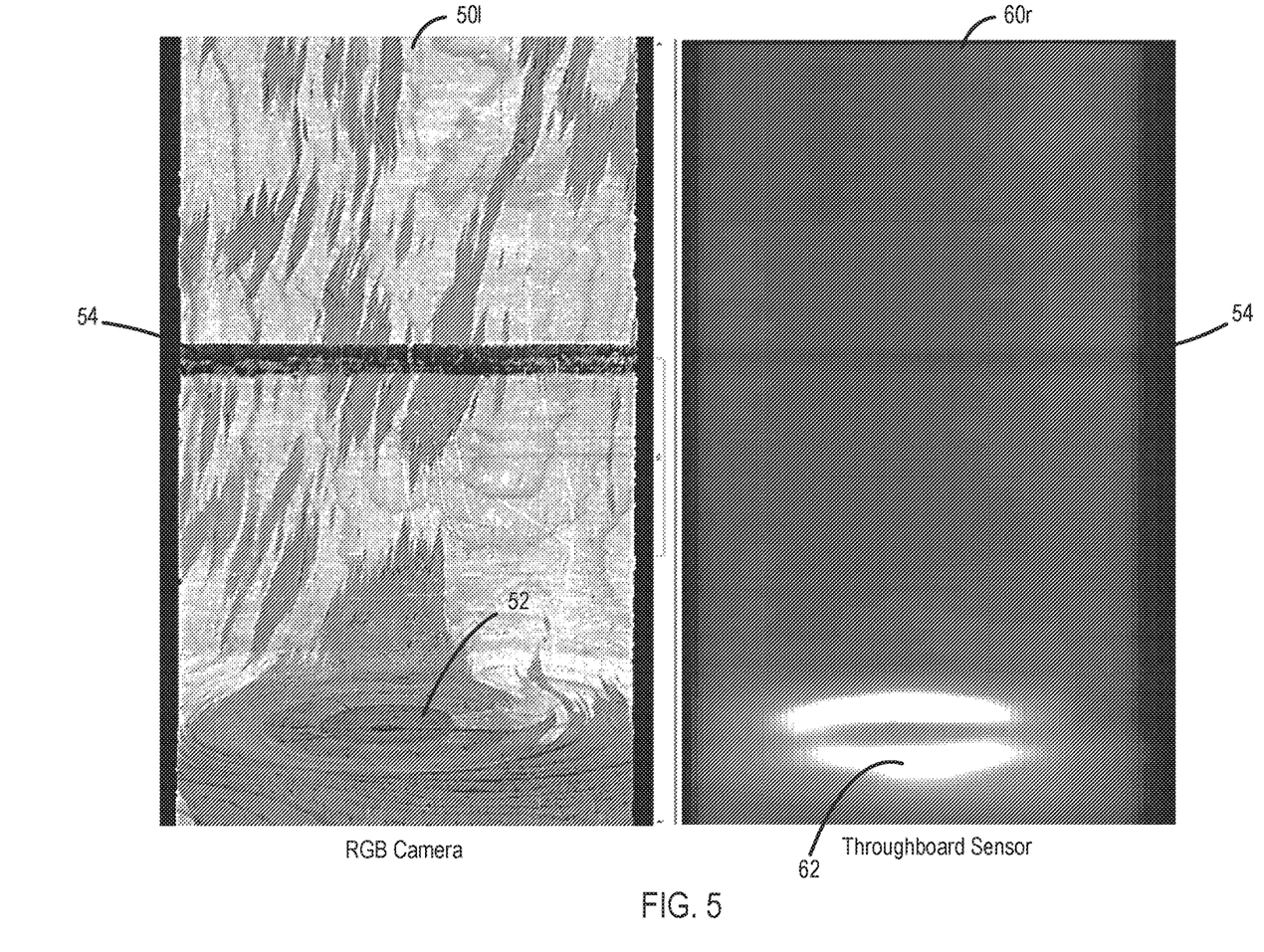

FIG. 5 shows two side-by-side images of the wood specimen, left-side image 50l and a right-side image 60r produced by a Throughboard sensor. The Throughboard sensor is similar to an X-ray device but instead uses radio waves. The whiter regions 62 in the image represent denser wood material. The Throughboard sensor produces two images, one each of the top and bottom faces. The top face image is shown in FIG. 5.

Figure 6:
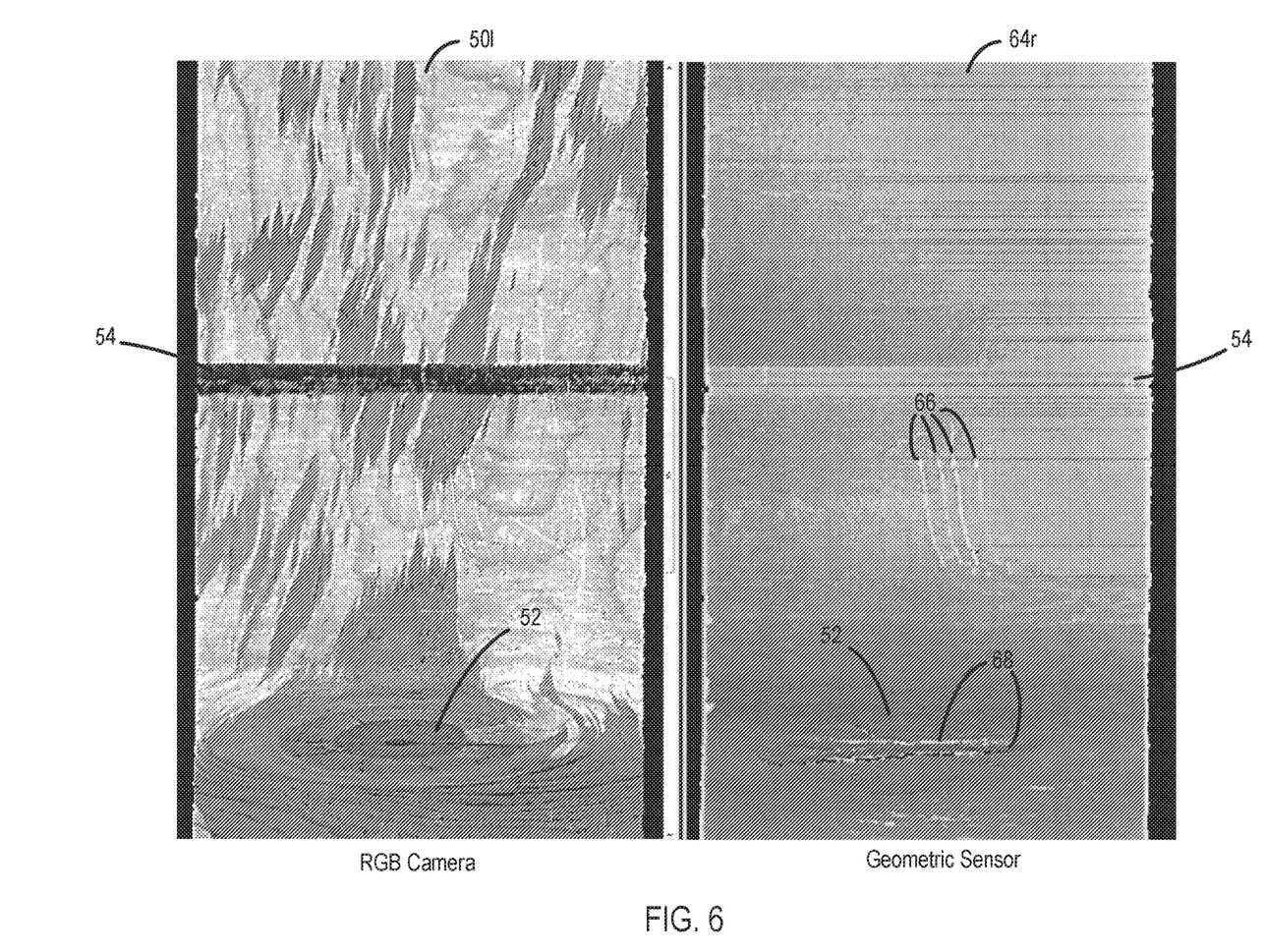

FIG. 6 shows two side-by-side images of the wood specimen, left-side image 50l and a right-side image 64r produced by a Geometric sensor. The Geometric sensor shows with 0.005 in. (0.127 mm) depth resolution four scratches 66 at the center of the image and cracks 68 in knot 52 at the bottom of the image. A greater degree of whiteness of the image indicates increased depth.

A process block 80 indicates that, upon deciding which image representing a particular layer of input pixel data shows the wood characteristics present in the wood specimen, the lumber grader labels the wood specimen by superimposing on the image a blob overlay that encompasses sets of pixels representing regions of the wood characteristics present. The corresponding pixels of each layer of input pixel data are spatially aligned; therefore, a blob overlay encompassing a region of the particular layer selected by the lumber grader translates to the same location in the images of the other input layers of pixel data.

Figure 7:
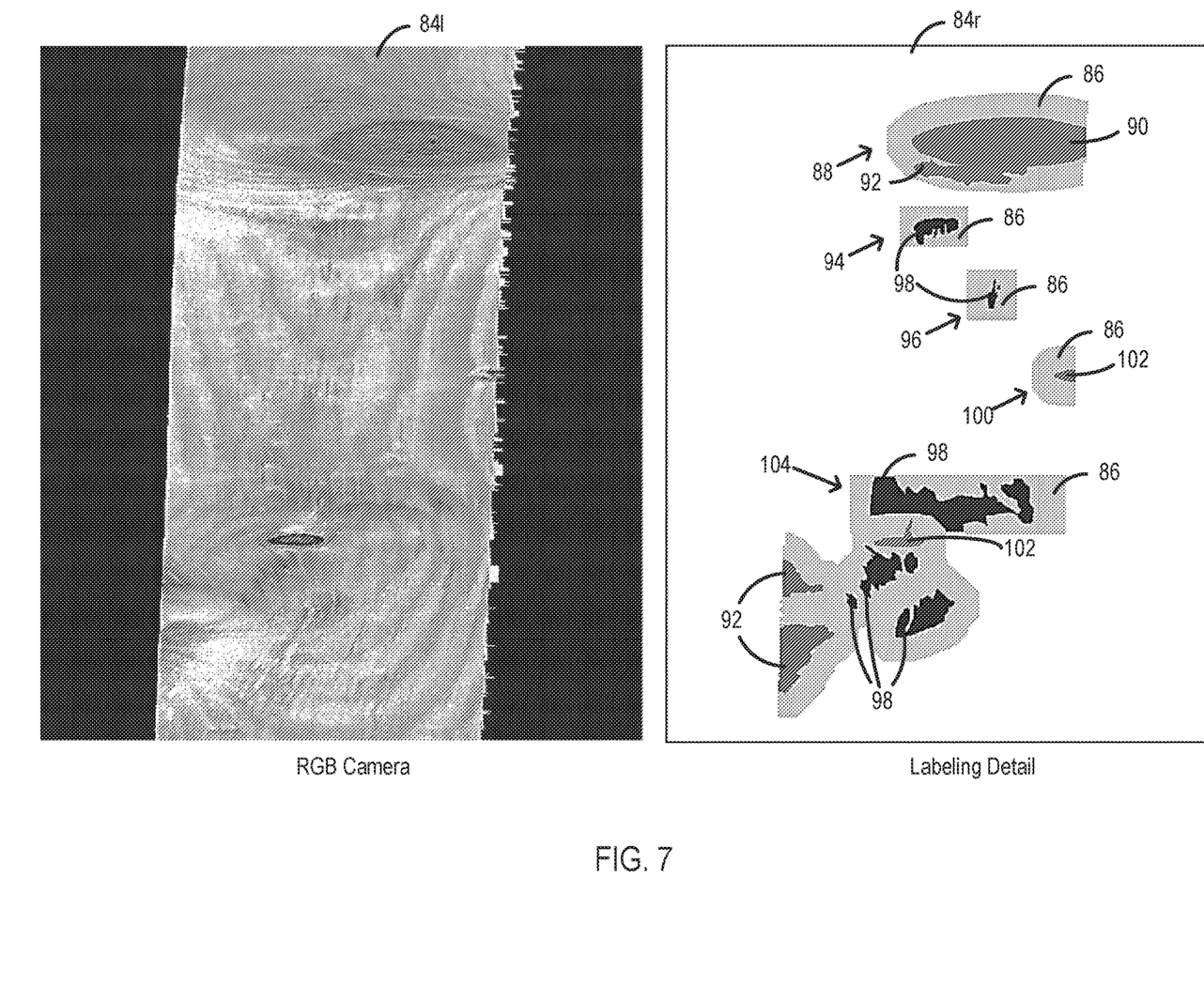
FIG. 7 presents two side-by-side images relating to a major surface of a wood specimen for showing labeling detail indicating classes of the wood characteristics of the wood specimen.

FIG. 7 presents two side-by-side images relating to a major surface of a wood specimen, a left-side image 84l produced by an RGB color camera (rendered as a gray scale view) and showing wood characteristics of the wood specimen, and right-side image 84r of wood characteristics showing labeling detail indicating classes of the wood characteristics. Right-side image 84r shows five regions in which wood characteristics are labeled. All wood characteristics in the five regions are encompassed by a clean wood characteristic 86. The white background in right-side image 84r represents a non-labeled wood material class because it is considered to be redundant to other labeling. A region 88 includes a red knot head 90 and torn grain 92. Each of regions 94 and 96 includes a kiln stain 98. A region 100 includes a dead knot 102. A region 104 includes two areas of torn grain 92, four areas of kiln stain 98, and dead knot 102.

A decision block 108 represents an inquiry whether another wood specimen of the selected species is available for analysis to determine classification of wood characteristics. If another wood specimen is available for analysis, the wood characteristics definition creation process resumes with scanning of the wood specimen, as indicated by process block 34. If there is no other wood specimen of the species available for analysis, a decision block 110 represents an inquiry whether a wood specimen of another wood species is available for selection. If there are wood specimens of another wood species to be analyzed, decision block 110 directs the wood characteristics definition creation process to process block 32, which starts the above-described wood characteristics definition creation process for each of the available wood specimens of the selected wood species. The wood characteristics definition creation process repeats for all wood samples of each wood species. Upon completion of the analysis of wood specimens to classify their wood characteristics, the machine learning training is complete and ends, as indicated by a process block 112.

The input layer pixel data representing the images of the wood specimens are applied to machine learning framework 12, which supports training processing unit 16. A set of deep learning algorithms developed to train a machine learning-based convolutional neural network on semantic segmentation is performed on training processing unit 16. A preferred convolutional neural network architecture particularly designed for segmentation is SegNet, which is a neural network architecture for semantic pixel-wise segmentation. The deep convolutional network architecture particularly designed for segmentation learns to decode or map low resolution image representations to pixel-wise predictions in a coarse-to-fine inference progression. Machine learning framework 12 functioning as an encoder classification network produces low resolution image representations from the wood specimen images represented by the input layer pixel data. The set of deep learning algorithms performing semantic segmentation on the input layer pixel data determines network learned weights for collections of pixels in the sets of pixels. The network learned weights reclassify the pixel data presented. The collections of pixels are encompassed by the edges and correspond to the regions of each of the wood specimens.

Upon completion of training and establishment of a set of network learned weights for the collections of pixels, milled board image data representing an unlabeled image of a milled board of wood are presented to machine learning framework 12. Milled board image data may be acquired by presenting the milled board of wood for processing by the GradeScan® system. Milled board raw image data produced by the multiple channel sensors include input layer pixel data. Milled board pixels of images defining wood characteristics of the milled board of wood are derived from each one of the multiple sensor channels. The raw milled board image data are applied to the trained convolutional neural network operating on inference processing unit 18 and supporting SegNet to perform semantic segmentation on the raw milled board image data. The performing of semantic segmentation determines, for the milled board pixels, probability values for use in forming a series of probability maps of the unlabeled image of the milled board of wood. Each probability map in the series corresponds to a different one of the classes of wood characteristics so that each milled board pixel of the milled board pixels has a probability value for each of the classes of wood characteristics.

Inference processing unit 18 derives from the probability values determined for the milled board pixels in the series of probability maps a solution identifying which ones of the milled board pixels belongs to classes of wood characteristics and specifying the classes to which the identified milled board pixels belong.

The output presented on a display is a rendering of the milled board of wood showing the actual shapes of the wood characteristics. The renderings indicate locations and boundaries of regions of the milled board of wood where inference processing unit 18 has identified the wood characteristics.

FIGS. 8, 9, 10, and 11 each present two side-by-side images demonstrating the solution determined by inference processing unit 18 identifying the wood characteristics of different milled boards of wood. In each of FIGS. 8, 9, 10, and 11, the left-side image is produced by an RGB color camera and shows a milled board as a gray scale view; and the right-side image highlights in the gray scale view the sizes and shapes of the wood characteristics identified in the solution determined by inference processing unit 18. The wood characteristics shown in the right-side view are preferably identified in different colors, but are represented as distinctive gray scale levels, to differentiate features of the wood characteristics present in the milled board.

Figure 8:
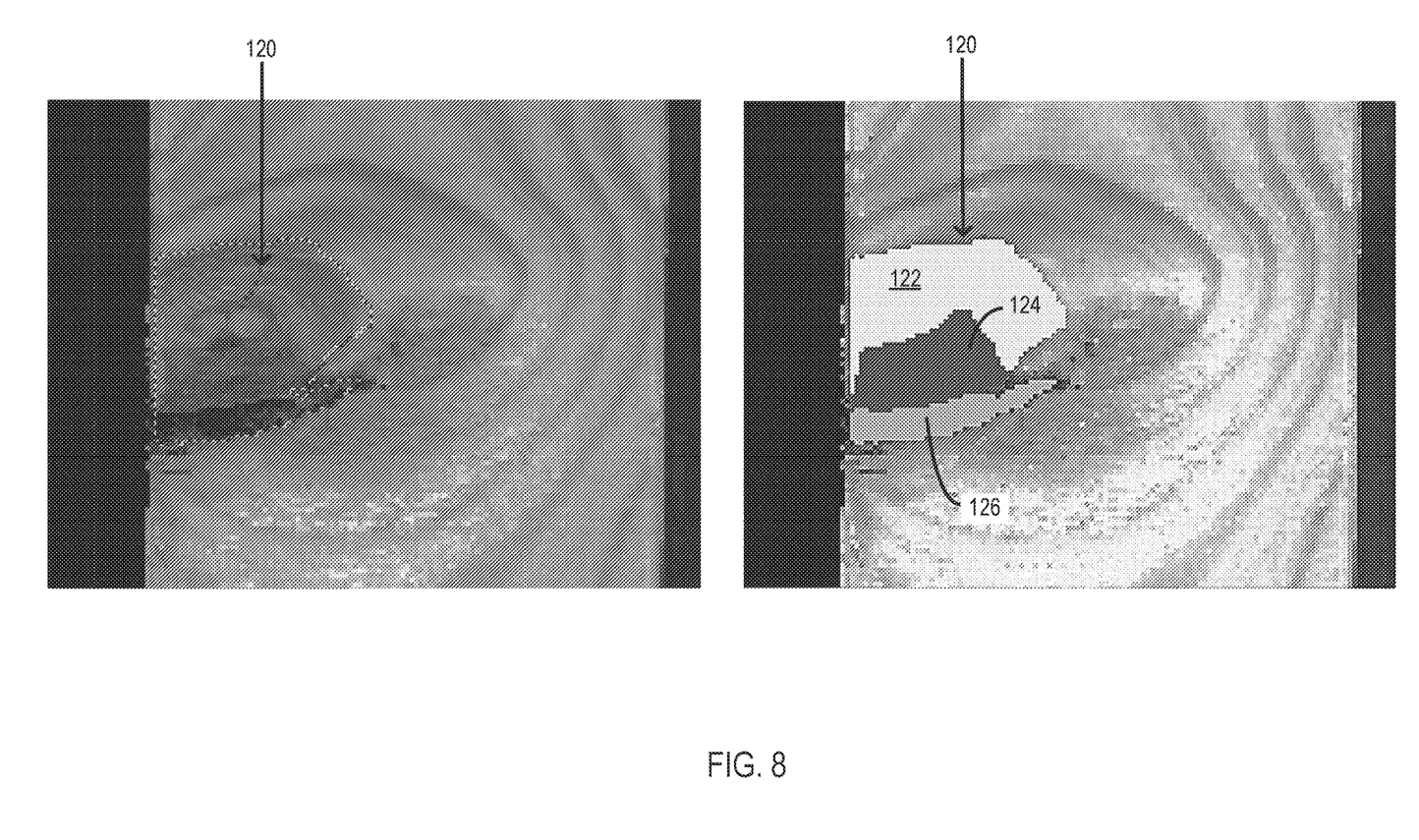
FIGS. 8, 9, 10, and 11 each present two side-by-side images demonstrating solutions determined by an inference processing unit in identifying the wood characteristics of different milled boards of wood.

FIG. 8 shows a knot 120, which, in the left-side view, is contained within a boundary indicated by a broken line. The right-side view shows three distinct parts of knot 120 representing three different characteristics. A top part 122 represents a blonde knot; a center part 124 represents a red knot head; and a bottom part 126 represents bark encasement. Because the solution differentiates separate parts of knot 120, the relative sizes of blonde knot 122 and bark encasement 126 enable determination of knot width during optimization. (If the bark encasement is smaller than the blonde knot, knot width would be measured from the total of the knot head and blonde knot regions.)

Figure 9:
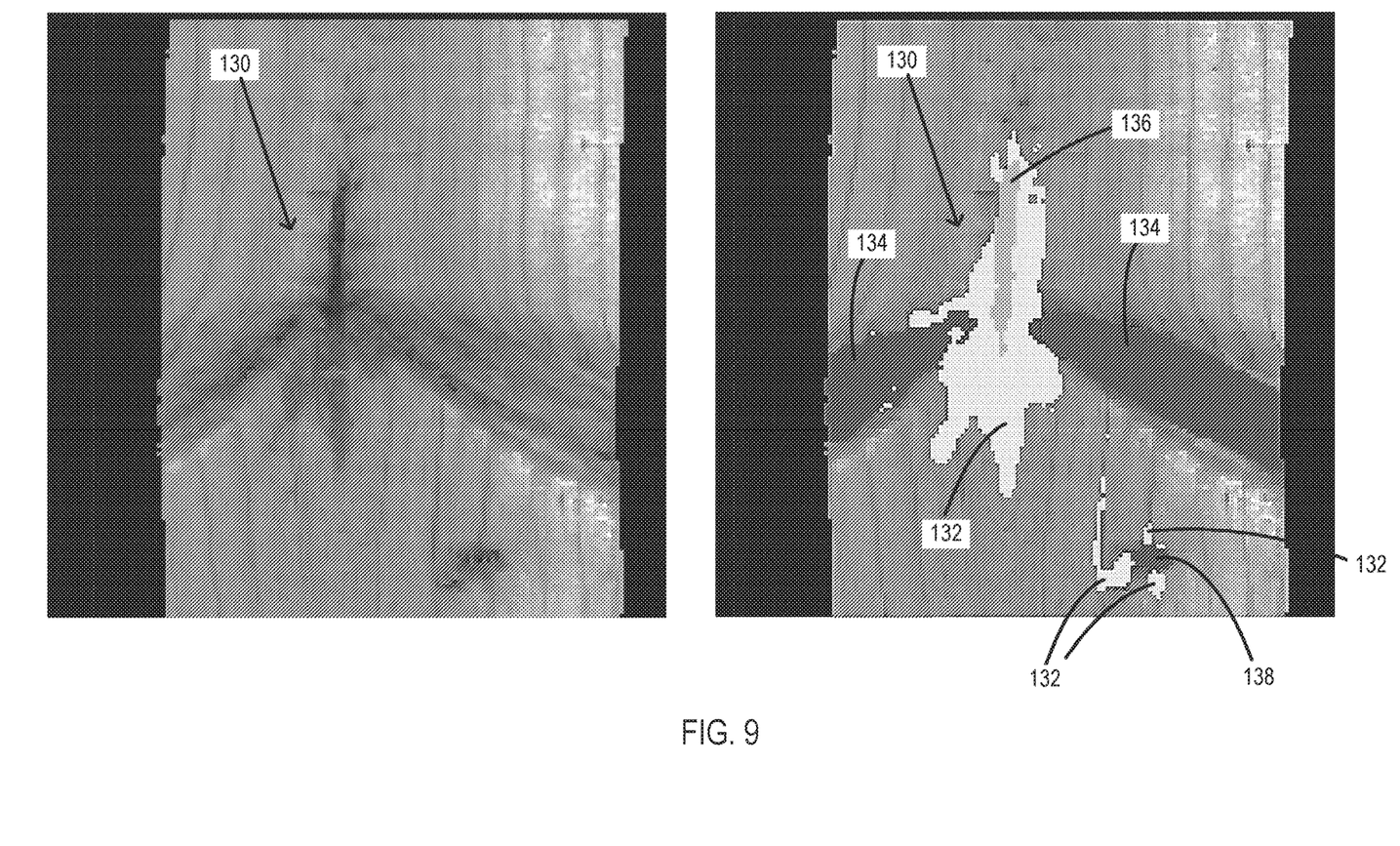

FIG. 9 demonstrates pattern recognition, which, in the left-side view, several knots appear to be connected in a knot spike pattern 130. The right-side view shows pitch (dried sap) 132 positioned between two spike knots 134 on either side of pitch 132. Pith 136 extends vertically within pitch 132. Because the solution differentiates the wood characteristics, the spike/pith/spike pattern does not connect the spike knots to each other. FIG. 9 also shows in the lower right-hand corner of the right-side view a dead knot head 138 partly surrounded by pitch 132.

Figure 10:
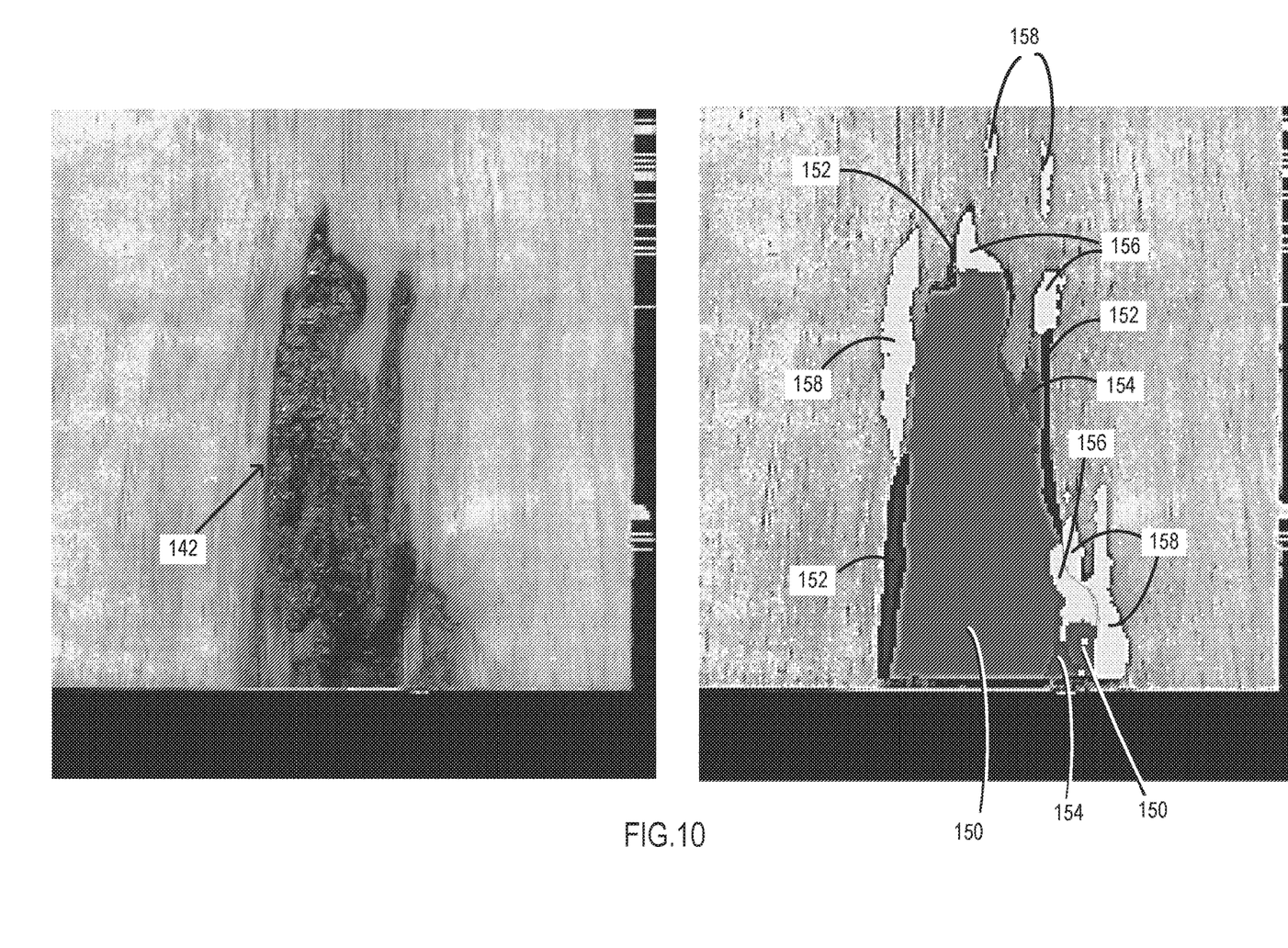

FIG. 10 shows an example of decay, stain, pitch, and bark pocket defects in a milled board. The left-side view shows a decayed major surface region 142 surrounded by pitch and stain. The right-side view shows a major region of decay 150 bordered by a narrow blue stain (fungus) 152 on left, right, and top portions of decay 150. Small areas of incipient decay 154, bark pockets 156, and pitch 158 appear around the border of decay 150.

Figure 11:
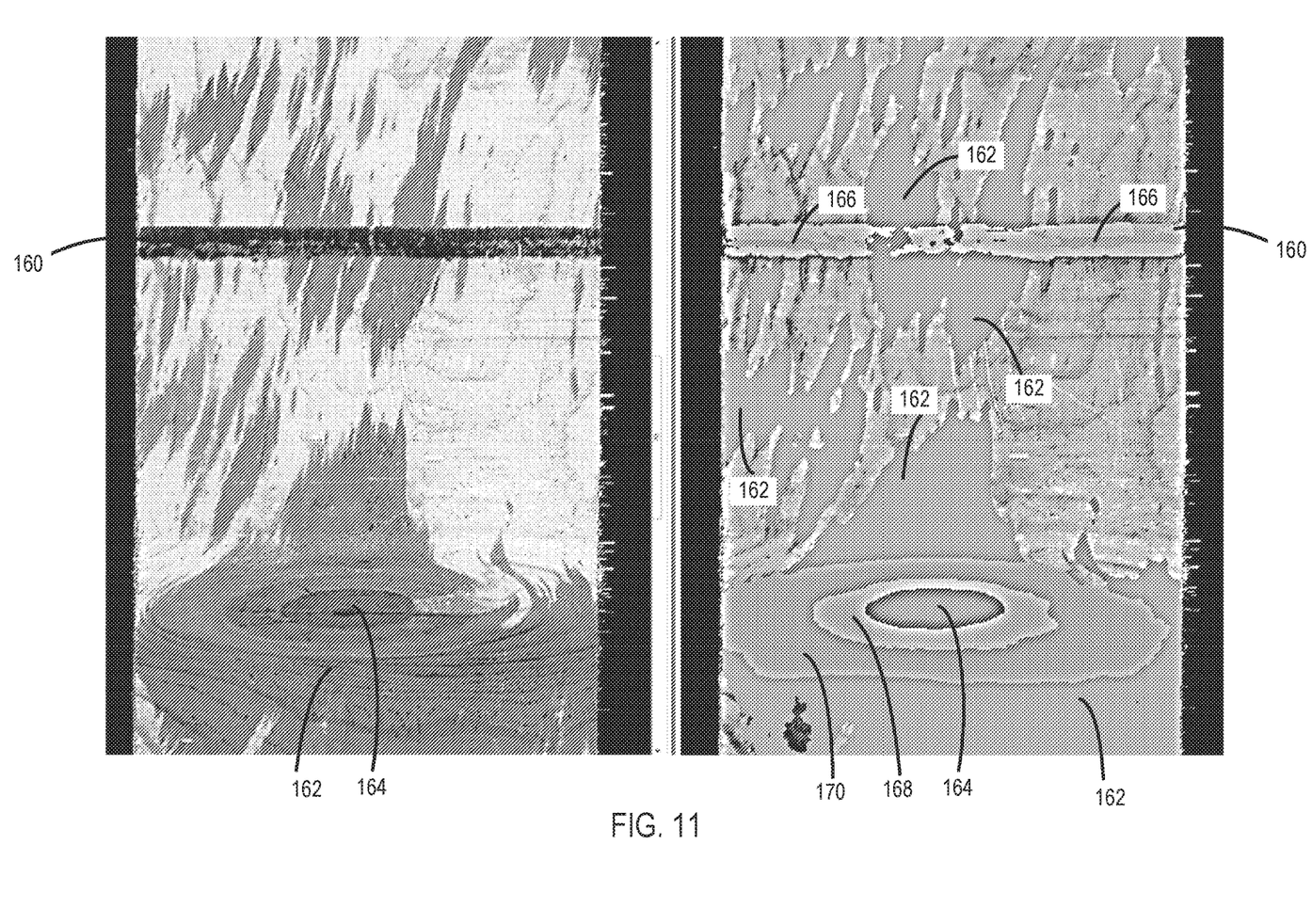

FIG. 11 shows an example of blue stain, planer burn, knot, kiln stain, and crossgrain defects in a milled board. The left-side view shows a horizontal planar burn 160 and patches of blue stain 162, one of which partly obscuring a red knot 164. The right-side view shows blue stain patches 162 covering about one-third of the board surface and planer burn 160 within which several kiln stains 166 are present. Red knot 164 is surrounded by a blonde knot ring 168, which is surrounded by crossgrain 170.

During the training and testing process, external settings, such as the size of a dotted line window around a sample defect, can be adjusted to fine tune the solution. The objective is to achieve, e.g., a 5% error upon conclusion of a testing process at a given prediction speed.

One program can be used to identify and locate an indefinite number of different defects simultaneously. The disclosed embodiment of the deep learning method provides a solution in constant time for equal area input boards. The implementations of prior art methods are characterized by longer solution times if a board is covered with many defects. With the disclosed method, if one knows the area of the largest board lumber product that will be graded, one can guarantee a solution time and need not specify extra computation power for the few times when an input board is covered in stain. SegNet is a feedforward neural network that facilitates solution time predictability. Semantic segmentation implemented in a deep cascade feed forward layered neural network can be performed as an alternative embodiment of the disclosed method that decreases solution time with less predictability in the detection of readily identifiable wood characteristics.

After the deep learning solution has been rendered, the board is directed to an optimizer system for grade assignment. A preferred optimizer system is the GradeScan® system.

Figure 12:
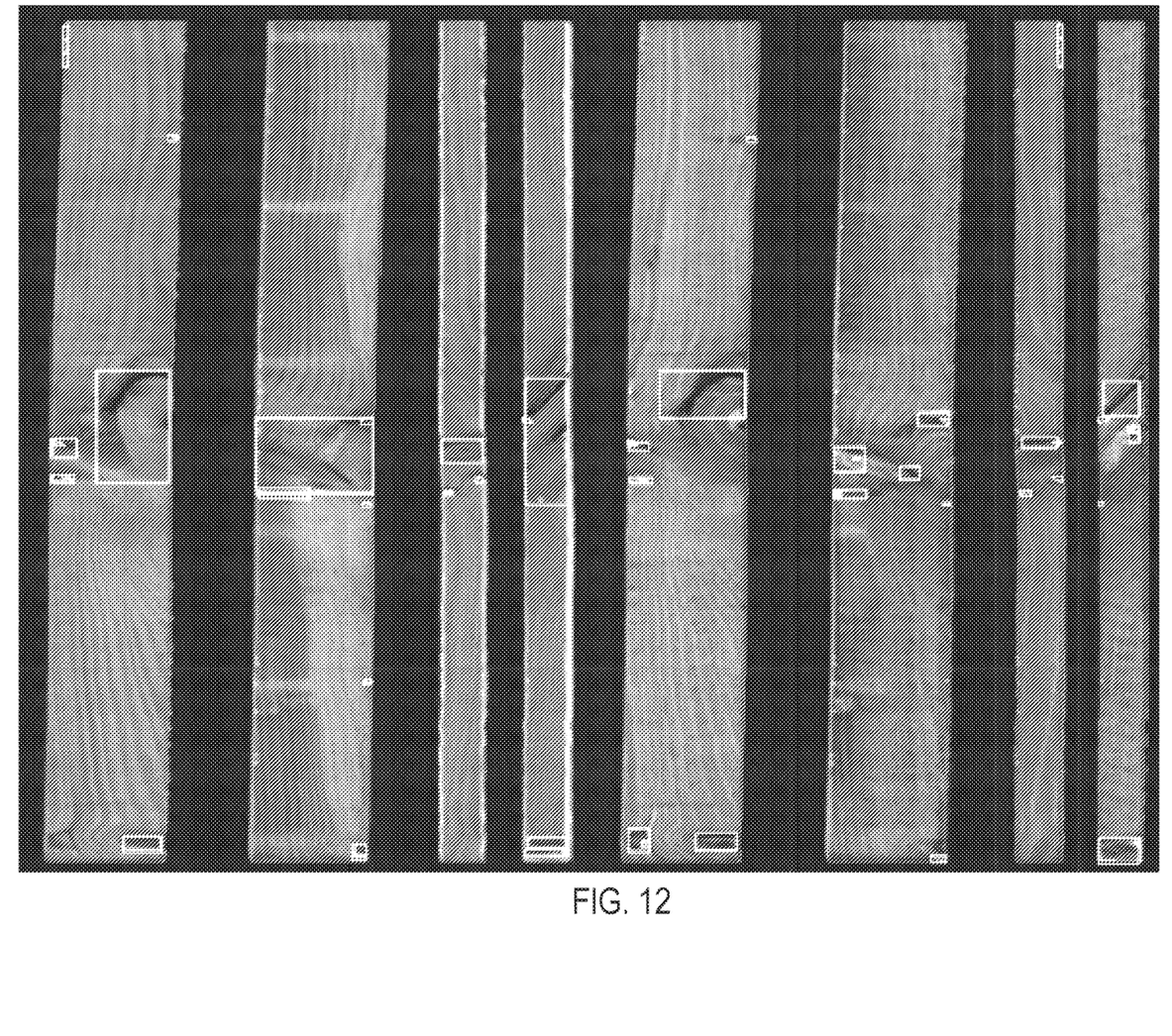
FIG. 12 presents two sets of images demonstrating a comparative relationship of results obtained in knot defect detection by the disclosed deep learning method and a prior art programming method.

FIG. 12 demonstrates, with respect to knot detection in board lumber grading, a comparative relationship of results obtained by the above-described deep learning method and by prior art programming implemented in a computer vision system. As stated above, the computer programmer of a computer vision system attempts to anticipate all possible presentations of knots and then gives explicit program instructions as to how to handle exceptional cases. This is in contrast to the disclosed deep learning method, in which the machine learning framework learns to detect defects from lumber grader presentation of examples of images showing the wood characteristics or defects to be detected.

FIG. 12 shows two sets of four images of the same board, presented side-by-side for comparison. The left-hand side set of four images represents, from left to right, the top, bottom, left side, and right side of the board analyzed by the disclosed deep learning method; and the right-hand side set of four images represents, from left to right, the top, bottom, left side, and right side of the board analyzed by a prior art hybrid rules-based and shallow neural network programming method.

The boxes around certain regions of the board indicate what the deep learning and prior art programming methods identified as knots. The long knot box located at the center on the top image analyzed by the deep learning method correctly identifies a knot, which was missed by the prior art programming method. One of the two knot boxes located at the bottom on the top image analyzed by the prior art programming method shows a false-positive decision, in which the left-side knot box erroneously identifies as a knot the round region of dark flat grain.

The advantages of the deep learning method are: accuracy of detection; reduction in false positives such as discoloration misidentified as a knot; same detection time consumed to determine a solution for boards of a given surface area, irrespective of the number of defects on any one of the boards; no requirement for constant software maintenance, in contrast to the prior art programming method and other previous machine learning methods, including shallow neural networks; improvement in small defect detection; and, with use of semantic segmentation neural network architecture, improvement in grading accuracy resulting from greater likelihood of detecting all defects on a board.

It will be obvious to those having skill in the art that many changes may be made to the details of the above-described embodiments without departing from the underlying principles of the invention, as indicated by the following claims.

The invention claimed is:

1. A computer implemented method of detecting defining characteristics of wood material to facilitate one or both of grading and optimizing board lumber by machine learning techniques, comprising:

creating a definition of wood characteristics learned from images of multiple wood specimens, the wood specimen images identifying the wood characteristics and represented by input layer pixel data derived from raw image data produced by automatic scanning of the multiple wood specimens, the input layer pixel data corresponding to sets of pixels representing regions of each of the wood specimen images, the input layer pixel data representing classes of the wood characteristics within specified boundaries of the regions at identified locations;

receiving, by a machine learning framework, the input layer pixel data, the machine learning framework supporting a training processing unit in which is performed a set of deep learning algorithms developed to train a machine learning-based convolutional neural network on semantic segmentation, the set of deep learning algorithms performing semantic segmentation on the input layer pixel data to determine edges in and network learned weights for collections of pixels in the sets of pixels, the collections of pixels encompassed by the edges and corresponding to the regions of each of the multiple wood specimens;

providing, to the machine learning framework, milled board image data representing a milled board of wood, the milled board image data including input layer pixel data produced by multiple sensor channels from each one of which are derived milled board pixels of images defining wood characteristics of the milled board of wood;

applying the milled board image data to the convolutional neural network operating on an inference processing unit, the convolutional neural network performing semantic segmentation on the milled board image data to determine, for the milled board pixels, probability values for use in forming a series of probability maps, each probability map in the series corresponding to a different one of the classes of wood characteristics so that each milled board pixel of the milled board pixels has a probability value for each of the classes of wood characteristics; and the inference processing unit deriving, from the probability values determined for the milled board pixels in the series of probability maps, a solution identifying which ones of the milled board pixels belong to classes of the wood characteristics and specifying the classes to which the identified milled board pixels belong, the solution derived by the inference processing unit being developed in constant time for equal area input milled boards of wood, irrespective of how many classes of the wood characteristics are identified on the milled board of wood.

2. The method of claim 1, further comprising providing a rendering of the milled board of wood, the rendering identifying locations and boundaries of the milled board pixels representing the classes of wood characteristics of the milled board of wood.

3. The method of claim 2, in which the rendering provided as an output includes a box encompassing and thereby indicating a region of the milled board of wood identifying one of the wood characteristics.

4. The method of claim 1, in which the inference processing unit includes a graphics processing unit (GPU), an application specific integrated circuit (ASIC), or a field programmable gate array (FPGA) for forming the series of probability maps.

5. The method of claim 1, in which the definition of wood characteristics includes classes of defects.

6. The method of claim 5, in which classes of defects include knot qualities.

7. The method of claim 1, in which the solution is derived for grading board lumber that is inspected in an industrial environment.

8. The method of claim 1, in which the inference processing unit includes a central processing unit (CPU) for deriving the solution from the series of probability maps formed.

9. The method of claim 1, in which the regions identifying locations of the wood characteristics are labeled by blob overlays placed around the regions on the wood specimen images.

10. The method of claim 6, in which the knot qualities include one or more of Red, Dead, Blonde, Decayed, Bark Encasement, and Slough to each of which deep learning is applied.

* * * * *

UNITED STATES PATENT AND TRADEMARK OFFICE
CERTIFICATE OF CORRECTION

PATENT NO. : 10,571,454 B2  
APPLICATION NO. : 16/082103  
DATED : February 25, 2020  
INVENTOR(S) : Narasimhan et al.

Page 1 of 1

It is certified that error appears in the above-identified patent and that said Letters Patent is hereby corrected as shown below:

In the Specification

Column 6, Line 45, change "fitness" to --thickness--.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*